United States Patent [19]

Waller et al.

[11] 4,297,341

[45] Oct. 27, 1981

[54] SPERMICIDAL COMPOSITION

[75] Inventors: Donald P. Waller, Elmhurst; Lourens J. D. Zaneveld, Forest Park; Harry H. S. Fong, Glen Ellyn, all of Ill.

[73] Assignee: University of Illinois Foundation, Urbana, Ill.

[21] Appl. No.: 148,567

[22] Filed: May 9, 1980

[51] Int. Cl.³ .................... A61K 31/11; A61K 31/79
[52] U.S. Cl. .................................... 424/80; 424/333; 424/DIG.14
[58] Field of Search .................. 424/80, 333, DIG. 14

[56] References Cited

U.S. PATENT DOCUMENTS 2,918,411 12/1959 Hill ........................................ 424/80
2,973,300 2/1961 Farrar et al. ......................... 424/80

OTHER PUBLICATIONS

Chinese Med. J. 4:417–428 (1978).
Merck Index, 9th Ed.; 1976; p. 588, para. 4377.

Primary Examiner—Leonard Schenkman
Attorney, Agent, or Firm—Mathew L. Kalinowski

[57] ABSTRACT

A water-soluble complex comprising polyvinylpyrrolidone and gossypol is an effective spermicide.

4 Claims, No Drawings

SPERMICIDAL COMPOSITION

This invention relates to spermicidal compositions and to methods for preparing such compositions. More particularly, this invention relates to complexes of water-soluble polymers and gossypol that exhibit spermicidal activity. In a specific aspect, this invention relates to vaginal contraceptives comprising a complex of polyvinylpyrrolidone and gossypol.

Gossypol, a disesquiterpene aldehyde obtained from the cotton plant, has the formula:

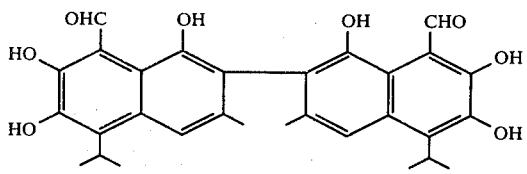

In a recent publication from the People's Republic of China, gossypol was reported to be an oral male anti-fertility agent (Anon., A New Anti-fertility Agent for Males, Chinese Med. J. 4:417–28, 1978). In the early stages of gossypol treatment, motility of ejaculated spermatozoa was reduced; in later stages, the total number of spermatazoa present was found to be less than 4 million/ml in ejaculates, which was taken as the criterion of anti-fertility. It was further reported that gossypol caused a degeneration of germ cells in the seminiferous tubules of man and animals when administered orally, leading to a complete absence of spermatogenesis.

Conventional, widely used vaginal contraceptives contain nonoxynol-9 as the spermicidal agent, which is a detergent and which was recently shown to be potentially toxic to the liver (Chvapil, M. et al., New Data on the Pharmokinetics of Nonoxynol-9, Vaginal Contraception, New Developments, Harper and Row, New York, pp 165–74, 1979).

Accordingly, it is an object of this invention to provide low-toxicity contraceptives containing gossypol as the spermicidal agent.

Another object of this invention is to provide a spermicidal complex comprising a water-soluble polymer and gossypol.

Still another object is to provide a vaginal contraceptive comprising a complex of polyvinylpyrrolidone and a spermicidally effective amount of gossypol.

These and other objects will become apparent as description of the invention proceeds.

In accordance with this invention it has been found that an effective spermicidal composition is formed when a water-soluble polymer is admixed with gossypol. Suitable water-soluble polymers are essentially non-toxic and readily form complexes with gossypol. Polyvinylpyrrolidone, a widely available, water-soluble polymer, can be used to particular advantage. The complex forms when a solution of the polymer and a solution of gossypol are mixed at ambient temperatures. Quantities of polymer and gossypol are chosen, for example, to provide a water-soluble complex containing from about 90% to about 50% by weight of the polymer and from about 10% to about 50% by weight of gossypol. The polymer-gossypol complex is then dried and formulated in spermicidally effective amount with a pharmaceutically acceptable carrier for use as a vaginal contraceptive.

DESCRIPTION OF THE PREFERRED EMBODIMENTS

The invention is further illustrated by reference to the following procedures and examples.

Gossypol acetic acid was obtained from the U.S. Department of Agriculture. Analytically pure gossypol was prepared from the acetic acid adduct by the method of Campbell et al., J. Amer. Chem. Soc. 59, 1723–38(1937). In the process, the adduct is dissolved in peroxide-free ether, mixed with aqueous sodium bisulfite solution (0.4%) and heated at 50° C. The resultant solid is further purified by repeating the process and by crystallization of the final solid from a mixture of ether and petroleum ether.

Polyvinylpyrrolidone(PVP), having a molecular weight of 10,000 was obtained from commercial sources.

Gossypol-PVP coprecipitate was prepared by dissolving gossypol in a minimum volume of ether and diluting with methanol to provide a concentration of 0.01 g/ml in a solution containing no more than 1% ether. PVP was dissolved in a minimum volume of methanol and mixed with the gossypol solution at room temperature in proportion of 4.0 g PVP/1.0 g gossypol. The precipitated complex was dried in vacuo at 40° C. utilizing a rotary evaporator, initially set at half speed, then at full speed when the volume was minimal in order to form a precipitate having a fluffy consistency and essentially free of solvent.

For testing, solutions were prepared containing concentrations of from 1 to 40 mg/ml of gossypol-PVP in saline. For comparative testing, PVP dissolved in saline, and gossypol and gossypol-acetic acid adduct triturated with saline were prepared.

In vitro spermicidal activity was determined according to a modified method of Sander, F. V. et al., Hum. Fertil. 6:134-37, 153(1941). Human semen was obtained from volunteer donors on the day of testing. Evaluation of spermicidal activity was carried out by mixing 0.1 ml of semen with 0.5 ml of the test preparations. The two fluids were thoroughly mixed by alternately drawing into and forcibly expressing the mixture from a pipette as rapidly as possible five times. A drop of the mixture was immediately placed on a slide and at least five fields were microscopically observed under low power magnification (100 ×) for spermatozoa motility. Each test was carried out within a 20 second time period. If no motility of spermatozoa was observed, the test was completed. For samples shown not to be spermicidal at 20 seconds, a second drop of semen was placed on the slide at three minutes and again observed for sperm motility. Each test was repeated at least twice.

The test results are listed in the following table:

TABLE I

Anti-Motility Effects of PVP, Gossypol, and Gossypol Derivatives

| Ingredient | Conc. (mg/ml) | Motility at 20 sec. | Motility at 3 min. |
| --- | --- | --- | --- |
| PVP | 30 | + | + |
|  | 70 | + | + |
|  | 200 | + | + |
| Gossypol (Free) | 20 | + | + |
|  | 40 | + | + |
|  | 80 | + | + |
|  | 100 | + | + |

TABLE I-continued

Anti-Motility Effects of PVP, Gossypol, and Gossypol Derivatives

| Ingredient | Conc. (mg/ml) | Motility at 20 sec. | 3 min. |
|---|---|---|---|
|  | 150 | + | + |
| Gossypol- | 20 | + | + |
| Acetic Acid | 40 | + | + |
|  | 80 | + | + |
|  | 100 | + | + |
|  | 150 | + | + |
| Gossypol-PVP | 1 | + | + |
|  | 5 | + | − |
|  | 10 | + | − |
|  | 20 | + | − |
|  | 40 | − | − |

+ motile spermatazoa present
− no motile spermatozoa found

The tabulated data show that PVP in concentrations up to 200 mg/ml, gossypol in concentrations up to 150 mg/ml, and gossypol acetic acid in concentrations up to 150 mg/ml did not decrease sperm motility. Both gossypol and gossypol acetic acid are highly insoluble in water, which most likely is responsible for failure to cause sprem immobilization.

In contrast, gossypol-PVP complex in concentration as low as 5 mg/ml resulted in complete immobilization of all spermatozoa within 3 minutes, and with concentration of 40 mg/ml complete immobilization in 20 seconds. Thus the data clearly show that although PVP alone and gossypol alone have no spermicidal activity under the specified test conditions, the gossypol-PVP complex is a highly effective spermicide.

In the same test procedure, three vaginal contraceptive preparations containing nonoxynol-9 as the spermicidal agent and currently marketed in this country exhibited spermicidal properties equal to or less than that of the gossypol-PVP complex of this invention.

An evaluation of the in vivo post-coital, spermicidal activity in non-human primates of a vaginally inserted formulation of gossypol-PVP with gelatin (100 mg gossypol-PVP/1 ml gelatin) was perfomed utilizing the method of Zaneveld et al., Animal Testing for Potency of Vaginal Contraceptives, Vaginal Contraception, New Developments, Harper and Row, New York, pp 247-55(1979). The gossypol-PVP-gelatin formulation was vaginally inserted in three Macaca arctoides (stumptailed macacques). All animals were paired with males within five minutes after the insertion of the gossypol-PVP-gelatin formulation. Following an observed mating, the males were immediately separated from the females and a sample of vaginal fluid was obtained as soon as possible. The vaginal fluid was observed under a microscope for the presence and motility of spermatozoa. In all mated and treated animals, large numbers of spermatozoa were present; however, no motile spermatozoa were observed in the vaginal fluid of two animals, and only 15% motile spermatozoa in the third animal. These results demonstrate the in vivo post-coital, spermicidal activity of the gossypol-PVP-gelatin formulation.

Although this invention has been described in particular reference to certain preferred embodiments thereof, it is understood that variations and modifications can be effected within the spirit and scope of the appended claims. It is intended that all the material contained in the above description shall be interpreted in an illustrative and not in a limiting sense.

What is claimed is:

1. A spermicidal composition for vaginal application comprising the complex formed from about 90 to about 50% by weight of polyvinylpyrrolidone and from about 10 to about 50% by weight of gossypol.

2. The spermicidal composition of claim 1 including a pharmaceutically acceptable carrier.

3. The spermicidal composition of claim 2 wherein the complex contains about 80% by weight of polyvinylpyrrolidone and about 20% by weight of gossypol, the complex being admixed with saline carrier to provide a concentration of from about 5 to about 40 mg of the complex in 1 ml of saline.

4. The spermicidal composition of claim 2 wherein the complex contains about 80% by weight of polyvinylpyrrolidone and about 20% by weight of gossypol, the complex being admixed with a gelatin carrier in a concentration of about 100 mg of complex in about 1 ml of gelatin.

* * * * *